(12) United States Patent
Shelton, IV et al.

(10) Patent No.: US 9,700,311 B2
(45) Date of Patent: Jul. 11, 2017

(54) TISSUE INGROWTH MATERIALS AND METHOD OF USING THE SAME

(71) Applicant: Ethicon LLC, Guaynabo, PR (US)

(72) Inventors: Frederick E. Shelton, IV, Hillsboro, OH (US); Tamara S. V. Widenhouse, Clarksville, OH (US)

(73) Assignee: Ethicon LLC, Guaynabo, PR (US)

( * ) Notice: Subject to any disclaimer, the term of this patent is extended or adjusted under 35 U.S.C. 154(b) by 698 days.

(21) Appl. No.: 14/075,459

(22) Filed: Nov. 8, 2013

(65) Prior Publication Data

US 2015/0129634 A1    May 14, 2015

(51) Int. Cl.
   *A61B 17/072*    (2006.01)
   *A61B 17/068*    (2006.01)
   (Continued)

(52) U.S. Cl.
   CPC ...... *A61B 17/068* (2013.01); *A61B 17/07207* (2013.01); *A61B 17/07292* (2013.01); *A61B 17/115* (2013.01); *A61B 2017/0046* (2013.01); *A61B 2017/00893* (2013.01); *A61B 2017/00898* (2013.01); *A61B 2017/00938* (2013.01); *A61B 2017/00942* (2013.01); *A61B 2017/07214* (2013.01)

(58) Field of Classification Search
   CPC . A61B 17/068; A61B 17/0686; A61B 17/072; A61B 17/07207; A61B 17/07292; A61B 17/115; A61B 17/1155; A61B 2017/00884; A61B 2017/00893; A61B 2017/07214; A61B 2017/00898
   USPC .......... 227/175.1, 176.1, 180.1, 19; 606/139, 606/143, 151, 215, 219, 148, 153, 154, 606/214
   See application file for complete search history.

(56) References Cited

U.S. PATENT DOCUMENTS 5,698,213 A    12/1997    Jamiolkowski et al.
5,700,583 A    12/1997    Jamiolkowski et al.
(Continued)

FOREIGN PATENT DOCUMENTS

EP    1442757 A1    8/2004
WO    2006023578 A2    3/2006
(Continued)

OTHER PUBLICATIONS

European Search Report for Application No. 14192311.0, 6 pages, dated Apr. 21, 2015.
(Continued)

*Primary Examiner* — Scott A. Smith
(74) *Attorney, Agent, or Firm* — Mintz Levin Cohn Ferris Glovsky and Popeo, P.C.

(57) ABSTRACT

Implantable materials for use with end effectors like surgical stapling devices, and methods for using the same, are generally provided. In some embodiments, adjunct materials for use with surgical staplers are provided. For example, a kit for stapling tissue is provided that can include a surgical stapler having an end effector. The end effector can have first and second jaws. The kit can include an adjunct material having hydrophobic surface regions and hydrophilic surface regions and the adjunct material can be configured to mate to at least one of the jaws of the end effector. Other implants, devices, and methods for surgical stapling are also provided.

19 Claims, 13 Drawing Sheets

(51) Int. Cl.
 *A61B 17/00* (2006.01)
 *A61B 17/115* (2006.01)

(56) References Cited

U.S. PATENT DOCUMENTS

| | | | |
|---|---|---|---|
| 6,273,897 B1* | 8/2001 | Dalessandro | A61B 17/07207 606/139 |
| 6,309,423 B2* | 10/2001 | Hayes | A61B 17/072 428/293.4 |
| 7,143,924 B2 | 12/2006 | Scirica et al. | |
| 7,143,925 B2 | 12/2006 | Shelton, IV et al. | |
| 7,772,352 B2 | 8/2010 | Bezwada | |
| 8,062,330 B2* | 11/2011 | Prommersberger | A61B 17/07207 227/175.1 |
| 8,317,070 B2 | 11/2012 | Hueil et al. | |
| 8,393,514 B2 | 3/2013 | Shelton, IV et al. | |
| 8,551,058 B2 | 10/2013 | Measamer et al. | |
| 2002/0165563 A1* | 11/2002 | Grant | A61B 17/072 606/151 |
| 2005/0059996 A1* | 3/2005 | Bauman | A61B 17/072 606/215 |
| 2006/0257458 A1 | 11/2006 | Gorman et al. | |
| 2007/0179528 A1* | 8/2007 | Soltz | A61B 17/072 606/219 |
| 2008/0114385 A1* | 5/2008 | Byrum | A61B 17/11 606/154 |
| 2008/0140115 A1* | 6/2008 | Stopek | A61B 17/068 606/219 |
| 2008/0161831 A1* | 7/2008 | Bauman | A61B 17/072 606/148 |
| 2008/0188766 A1* | 8/2008 | Gertner | A61F 5/0086 600/561 |
| 2009/0001122 A1* | 1/2009 | Prommersberger | A61B 17/07207 227/176.1 |
| 2009/0234193 A1 | 9/2009 | Weisenburgh, II et al. | |
| 2009/0270686 A1 | 10/2009 | Duke et al. | |
| 2010/0331880 A1* | 12/2010 | Stopek | A61B 17/0644 606/219 |
| 2011/0192882 A1 | 8/2011 | Hess et al. | |
| 2012/0024934 A1 | 2/2012 | Shelton, IV et al. | |
| 2012/0031950 A1* | 2/2012 | Prommersberger | A61B 17/07207 227/176.1 |
| 2012/0080335 A1 | 4/2012 | Shelton, IV et al. | |
| 2012/0083835 A1 | 4/2012 | Shelton, IV et al. | |
| 2012/0241491 A1* | 9/2012 | Aldridge | A61B 17/07292 227/175.1 |
| 2013/0112733 A1 | 5/2013 | Aranyi et al. | |
| 2013/0146642 A1 | 6/2013 | Shelton, IV et al. | |
| 2013/0153641 A1 | 6/2013 | Shelton, IV et al. | |
| 2013/0161374 A1 | 6/2013 | Swayze et al. | |
| 2013/0209659 A1* | 8/2013 | Racenet | A61L 31/145 427/2.1 |
| 2013/0256365 A1 | 10/2013 | Shelton, IV et al. | |
| 2013/0256372 A1 | 10/2013 | Baxter, III et al. | |
| 2013/0256376 A1 | 10/2013 | Barton et al. | |
| 2013/0256377 A1 | 10/2013 | Schmid et al. | |
| 2014/0158741 A1 | 6/2014 | Woodard, Jr. et al. | |
| 2015/0173756 A1 | 6/2015 | Baxter, III et al. | |
| 2015/0272575 A1 | 10/2015 | Leimbach et al. | |

FOREIGN PATENT DOCUMENTS

| | | |
|---|---|---|
| WO | 2013148773 A1 | 10/2013 |
| WO | 2014016819 A1 | 1/2014 |

OTHER PUBLICATIONS

U.S. Appl. No. 14/074,810, filed Nov. 8, 2013.
U.S. Appl. No. 14/074,884, filed Nov. 8, 2013.
U.S. Appl. No. 14/074,902, filed Nov. 8, 2013.
U.S. Appl. No. 14/075,438, filed Nov. 8, 2013.
Chen et al. "Elastomeric Biomaterials for Tissue Engineering." Prog. Polymer. Sci. 38(2013):584-671.
Lim et al. "Fabrication and Evaluation of Poly(epsilon-caprolactone)/Silk Fibroin Blend Nanofibrous Scaffold." Biopolymers. 97(2012):265-275.
U.S. Appl. No. 13/763,192, filed Feb. 8, 2013.
U.S. Appl. No. 14/300,793, filed Jun. 10, 2014.
U.S. Appl. No. 14/300,799, filed Jun. 10, 2014.
U.S. Appl. No. 14/300,801, filed Jun. 10, 2014.
U.S. Appl. No. 14/300,804, filed Jun. 10, 2014.
U.S. Appl. No. 14/300,807, filed Jun. 10, 2014.
U.S. Appl. No. 14/300,811, filed Jun. 10, 2014.
U.S. Appl. No. 14/300,815, filed Jun. 10, 2014.
U.S. Appl. No. 14/300,817, filed Jun. 10, 2014.
U.S. Appl. No. 14/300,819, filed Jun. 10, 2014.
U.S. Appl. No. 14/300,820, filed Jun. 10, 2014.
U.S. Appl. No. 14/300,954, filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.

* cited by examiner

TISSUE INGROWTH MATERIALS AND METHOD OF USING THE SAME

FIELD

The present invention relates to surgical instruments, and in particular to methods, devices, and components thereof for cutting and stapling tissue.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Implantable materials for use with end effectors like surgical stapling devices, and methods for using the same, are generally provided. In some embodiments, adjunct materials for use with surgical staplers are provided. For example, a kit for stapling tissue is provided that can include a surgical stapler having an end effector. The end effector can have first and second jaws. The kit can include an adjunct material having hydrophobic surface regions and hydrophilic surface regions and the adjunct material can be configured to mate to at least one of the jaws of the end effector.

In some embodiments, the adjunct material can be formed from a hydrophobic polymer and/or copolymer that is treated with a hydrophilic polymer. The adjunct material can also be formed from a hydrophobic polymer and/or copolymer that is treated with an acid or base. In some embodiments, the adjunct material can be formed from a hydrophobic polymer that is treated by covalently bonding hydrophilic moieties onto at least a portion of the hydrophobic polymer. The hydrophilic surface region can be laminated to the hydrophobic surface region. The adjunct material can include an absorbable polymer. In some embodiments, the adjunct material can include a copolymer selected from the group consisting of polyglycolic acid/polycaprolactone and polylactic acid/polycaprolactone. Also, the adjunct material can include a foam.

In some exemplary embodiments a staple cartridge assembly for use with a surgical stapler, can include a cartridge body having a plurality of staples disposed therein and an adjunct material configured to be coupled to the cartridge and configured to be securely attached to tissue by staples in the cartridge. The adjunct material can have a hydrophobic surface region and an opposite hydrophilic surface region. In some embodiments, the adjunct material can be formed from a hydrophobic polymer and/or copolymer that is treated with a hydrophilic polymer. The adjunct material can also be formed from a hydrophobic polymer and/or copolymer that is treated with an acid or base. In some embodiments, the adjunct material can be formed from a hydrophobic polymer that is treated by covalently bonding hydrophilic moieties onto at least a portion of the hydrophobic polymer. In some embodiments, the hydrophilic surface region can be configured to directly contact tissue when secured to tissue by the staples such that tissue ingrowth is encouraged. The adjunct material can include a copolymer selected from the group consisting of polyglycolic acid/polycaprolactone and polylactic acid/polycaprolactone. In some embodiments, the adjunct material include a polyglycolic acid/polycaprolactone copolymer having polyethylene glycol and/or poloxamer repeat units. The adjunct material can include at least one of a biologic material, an electrically charged material, and an internal support structure. Also, the adjunct material can include a foam.

In other aspects, a method for stapling tissue is provided. The method can include attaching an adjunct material to an end effector on a surgical stapling device such that a hydrophobic surface on the adjunct material directly contacts the end effector. The method can also include engaging tissue between the jaws of the end effector such that a hydrophilic surface on the adjunct material directly contacts the tissue, and actuating the end effector to eject at least one staple from the end effector into the tissue. The at least one staple can extend through the adjunct material to attach the adjunct material to the tissue. In some embodiments, the adjunct material can include a polyglycolic acid/polycaprolactone copolymer having polyethylene glycol and/or poloxamer repeat units. Also, the hydrophilic surface can include a first layer of material and the hydrophobic surface can be a coating that is laminated to the first layer of material.

BRIEF DESCRIPTION OF THE DRAWINGS

The invention will be more fully understood from the following detailed description taken in conjunction with the accompanying drawings, in which.

DETAILED DESCRIPTION

Figure 1:
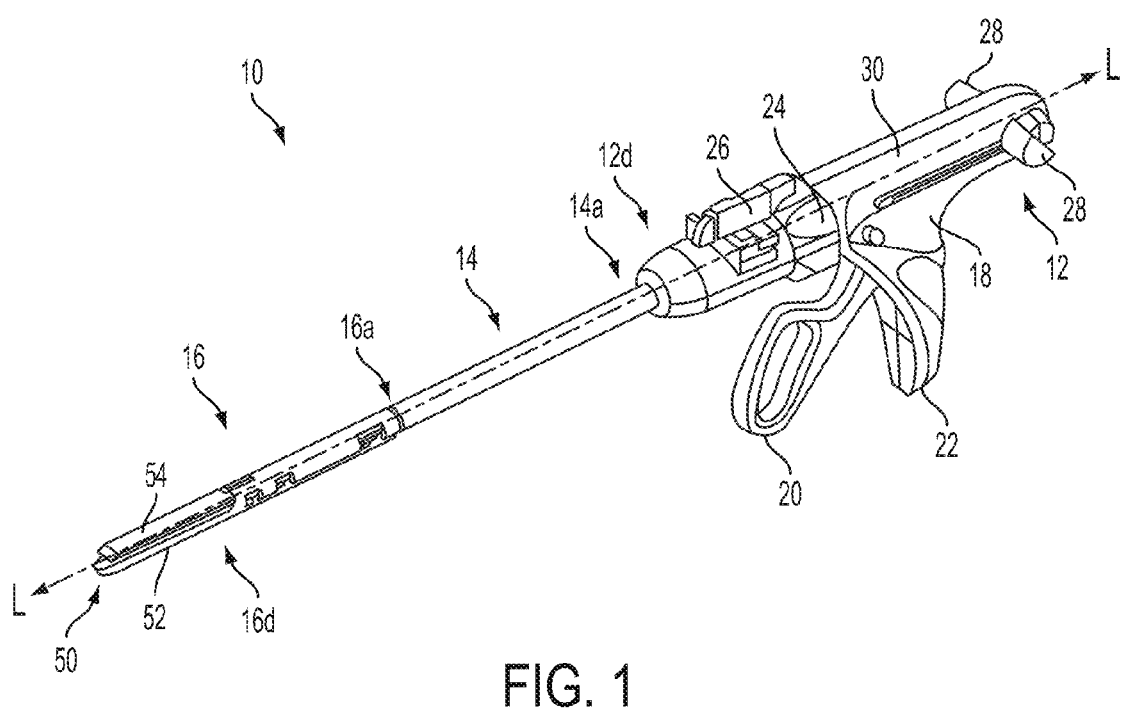
FIG. 1 is a perspective view of one exemplary embodiment of a surgical instrument having an attachment portion attached to a distal end thereof.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjunct materials," in conjunction with surgical instruments to help improve surgical procedures. A person skilled in the art may refer to these types of materials as adjunct materials. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the material(s) can be used to help seal holes formed by staples as they are implanted into tissue, blood vessels, and various other objects or body parts. Further, the materials can be used to provide tissue reinforcement at the treatment site. Still further, the materials can help reduce inflammation, promote cell growth, and otherwise improve healing.

Surgical Stapling Instrument

Figure 2:
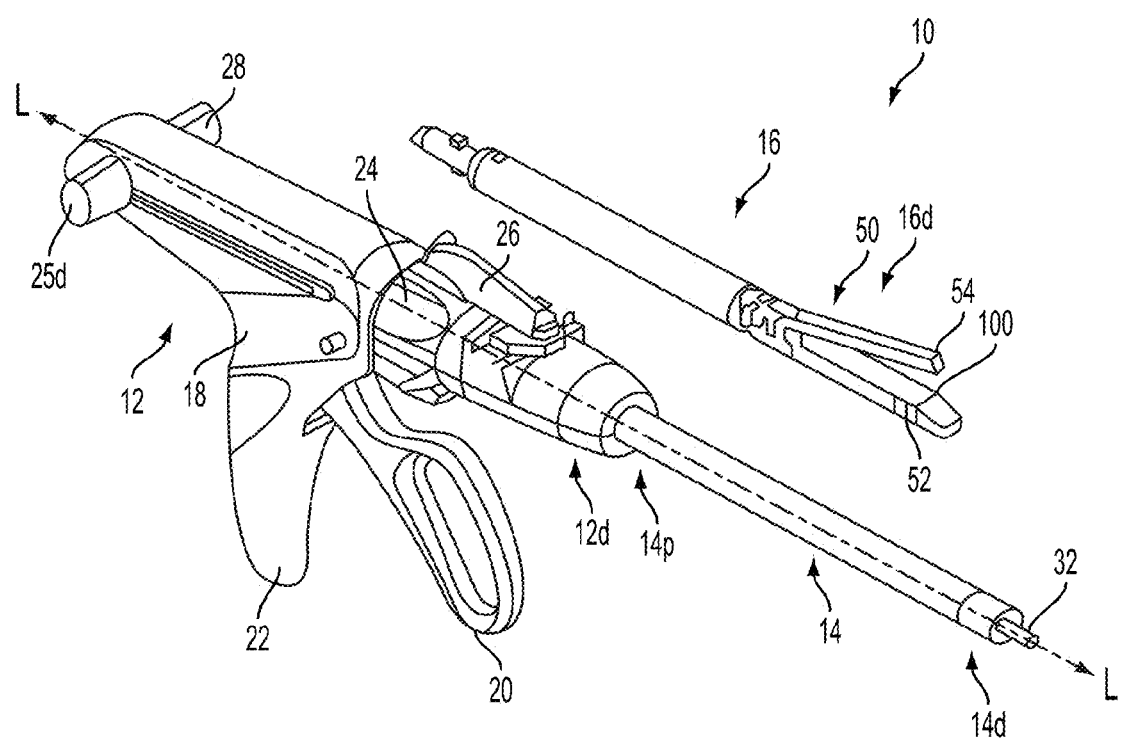
FIG. 2 is a perspective view of the surgical instrument of FIG. 1 with the attachment portion detached from a shaft of the instrument.

While a variety of surgical instruments can be used in conjunction with the adjunct materials disclosed herein, FIGS. 1 and 2 illustrate one, non-limiting exemplary embodiment of a surgical stapler 10 suitable for use with one or more adjunct materials. As shown the instrument 10 includes a handle assembly 12, a shaft 14 extending distally from a distal end 12d of the handle assembly 12, and an attachment portion 16 removably coupled to a distal end 14d of the shaft 14. Because the illustrated embodiment is a surgical stapler, a distal end 16d of the attachment portion 16 includes an end effector 50 having jaws 52, 54, although other types of end effectors can be used with the shaft 14, handle assembly 12, and components associated with the same. As shown, the surgical stapler includes opposed first and second jaws 52, 54 with the first, lower jaw 52 including an elongate channel 56 (FIG. 4) configured to support a staple cartridge 100, and the second, upper jaw 54 having an inner surface 58 (FIGS. 3, 4, and 6) that faces the lower jaw 52 and that is configured to operate as an anvil to help deploy staples of a staple cartridge. The jaws 52, 54 are configured to move relative to one another to clamp tissue or other objects disposed therebetween, and an axial drive assembly 80 (FIG. 11) can be configured to pass through at least a portion of the end effector 50 to eject the staples into the clamped tissue. In various embodiments a knife blade 81 can be associated with the axial drive assembly 80 to cut tissue during the stapling procedure.

Operation of the end effector 50 and drive assembly 80 can begin with input from a clinician at the handle assembly 12. The handle assembly 12 can have many different configurations designed to manipulate and operate the end effector associated therewith. In the illustrated embodiment, the handle assembly 12 has a pistol-grip type housing 18 with a variety of mechanical components disposed therein to operate various features of the instrument. For example, the handle assembly 12 can include mechanical components as part of a firing system actuated by a trigger 20. The trigger 20 can be biased to an open position with respect to a stationary handle 22, for instance by a torsion spring, and movement of the trigger 20 toward the stationary handle 22 can actuate the firing system to cause the axial drive assembly 80 to pass through at least a portion of the end effector 50 and eject staples from a staple cartridge disposed therein. A person skilled in the art will recognize various configurations of components for a firing system, mechanical or otherwise, that can be used to eject staples and/or cut tissue, and thus a detailed explanation of the same is unnecessary.

Other non-limiting examples of features that can be incorporated into the handle assembly 22 that affect manipulation and operation of an end effector associated therewith include a rotatable knob 24, an articulation lever 26, and retraction knobs 28. As shown, the rotatable knob 24 can be mounted on a forward end of a barrel portion 30 of the handle assembly 12 to facilitate rotation of the shaft 14 (or the attachment portion 16) with respect to the handle assembly 12 around a longitudinal axis L of the shaft 14. The actuation lever 26 can also be mounted on a forward end of the barrel portion 30, approximately adjacent to the rotatable knob 24. The lever 26 can be manipulated from side-to-side along a surface of the barrel portion 30 to facilitate reciprocal articulation of the end effector 50. One or more retraction knobs 28 can be movably positioned along the barrel portion 30 to return the drive assembly 80 to a retracted position, for example after the firing system has completed a firing stroke. As shown, the retraction knobs 28 move proximally toward a back end of the barrel portion 30 to retract components of the firing system, including the drive assembly 80.

Still other non-limiting examples of features that can be incorporated into the handle assembly 22 that affect manipulation and operation of an end effector associated therewith can include a firing lockout assembly, an anti-reverse clutch mechanism, and an emergency return button. A firing lockout assembly can be configured to prevent the firing system from being actuated at an undesirable time, such as when an end effector is not fully coupled to the instrument. An anti-reverse clutch mechanism can be configured to prevent components of the firing system from moving backwards when such backwards movement is undesirable, such as when the firing stroke has only been partially completed but temporarily stopped. An emergency return button can be configured to permit components of a firing system to be retracted before a firing stroke is completed, for instance in a case where completing the firing stroke may cause tissue to be undesirably cut. Although features such as a firing lockout assembly, an anti-reverse clutch mechanism, and an emergency return button are not explicitly illustrated in the instrument 10, a person skilled in the art will recognize a variety of configurations for each feature that can be incorporated into a handle assembly and/or other portions of a surgical stapler without departing from the spirit of the present disclosure. Additionally, some exemplary embodiments of features that can be incorporated into the handle assembly 12 are provided for in patents and patent applications incorporated by reference elsewhere in the present application.

The shaft 14 can be removably coupled to the distal end 12d of the handle assembly 12 at a proximal end 14p of the shaft 14, and a distal end 14d of the shaft 14 can be configured to receive the attachment portion 16. As shown, the shaft 14 is generally cylindrical and elongate, although any number of shapes and configurations can be used for the shaft, depending, at least in part, on the configurations of the other instrument components with which it is used and the type of procedure in which the instrument is used. For example, in some embodiments, a distal end of one shaft can have a particular configuration for receiving certain types of end effectors, while a distal end of another shaft can have a different configuration for receiving certain other types of end effectors. Components of the firing system, such as a control rod 32 (FIG. 2), can be disposed in the shaft 14 so that the components can reach the end effector 50 and drive assembly 80 to provide actuation of the same. For example, when the trigger 20 operates the firing system, the control rod 32 can be advanced distally through at least a portion of the shaft 14 to cause the jaws 52, 54 to collapse towards each other and/or to drive the drive assembly 80 distally through at least a portion of the end effector 50.

The shaft 14 can also include one or more sensors (not shown) and related components, such as electronic components to help operate and use the sensors (not shown). The sensors and related components can be configured to communicate to a clinician the type of end effector associated with the distal end 14d of the shaft 14, among other parameters. Likewise, the handle assembly 12 can include one or more sensors and related components configured to communicate to a clinician the type of end effector and/or shaft associated with the distal end 12d of the handle assembly 12. Accordingly, because a variety of shafts can be interchangeably coupled with the handle assembly 12 and a variety of end effectors having different configurations can be interchangeably coupled with various shafts, the sensors can help a clinician know which shaft and end effector are being used. Additionally, the information from the sensors can help a monitoring or control system associated with the instrument know which operation and measurement parameters are relevant to a clinician based on the type of shaft and end effector coupled to the handle assembly. For example, when the end effector is a stapler, information about the number of times the drive assembly 80 is fired may be relevant, and when the end effector is another type of end effector, such as a cutting device, the distance the cutting portion traveled may be relevant. The system can convey the appropriate information to the clinician based on the end effector that is sensed.

A person skilled in the art will recognize that various configurations of monitoring and control systems can be used in conjunction with the surgical instruments provided herein. For example, sensors associated with any of the end effector 50, the attachment portion 16, the shaft 14, and the handle assembly 12 can be configured to monitor other system parameters, and a monitoring or control system can communicate to a clinician the relevant other parameters based on the type of shaft or attachment portion associated with the handle assembly. Further details about sensors and related components, as well as monitoring and control systems, can be found in patents and patent applications incorporated by reference elsewhere in the present application.

Figure 3:
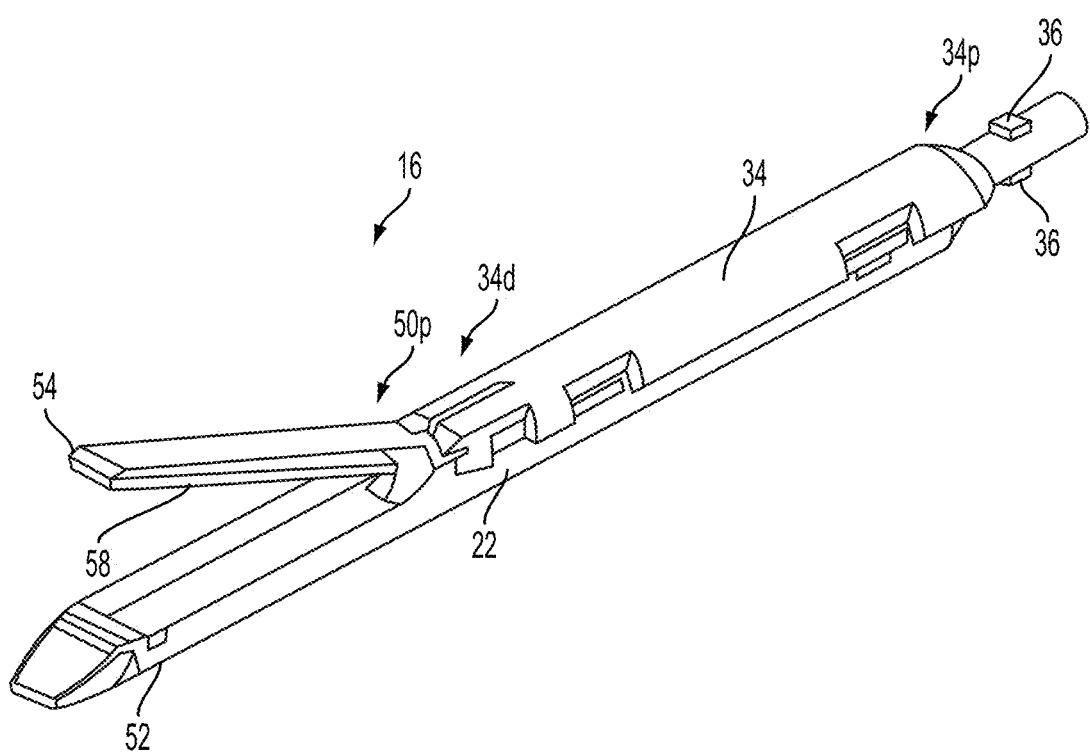
FIG. 3 is a perspective view of the attachment portion of FIG. 2 including at least one piece of adjunct material.

As shown in FIG. 3, the attachment portion 16 can include a proximal housing portion 34 at a proximal end 16p thereof and an end effector or tool 50 at a distal end 16d thereof. In the illustrated embodiment, the proximal housing portion 34 includes on a proximal end 34p thereof engagement nubs 36 for releasably engaging the shaft 14. The nubs 36 form a bayonet type coupling with the distal end 14d of the shaft 14. Besides nubs 36, any number of other complementary mating features can be used to allow the attachment portion 16 to be removably coupled to the shaft 14.

Figure 4:
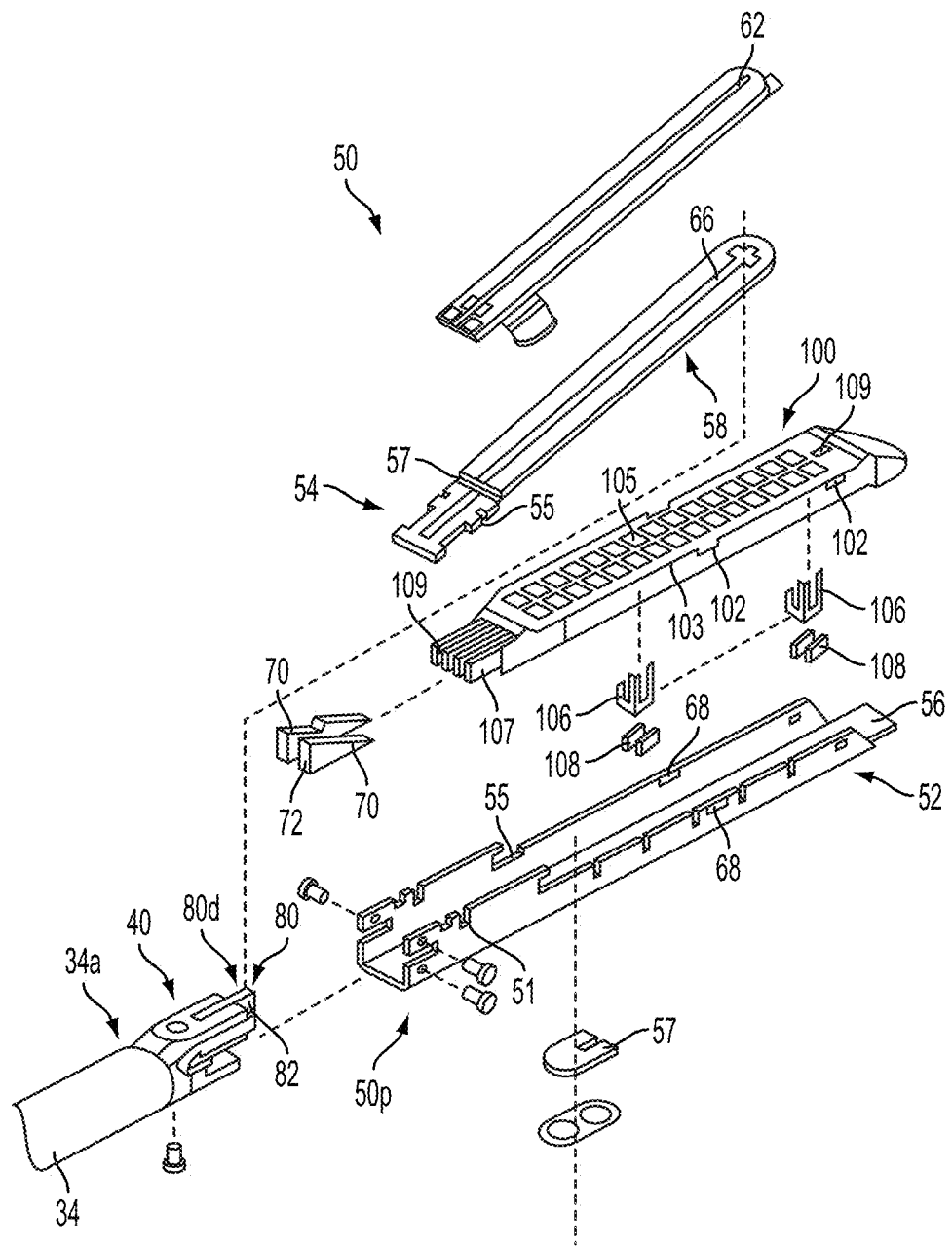
FIG. 4 is an exploded perspective view of the end effector of FIG. 3 with the adjunct material removed.

A distal end 34d of the proximal housing portion 34 can include a mounting assembly 40 pivotally secured thereto. As shown in FIG. 4, the mounting assembly 40 can be configured to receive a proximal end 50p of the end effector 50 such that pivotal movement of the mounting assembly 40 about an axis perpendicular to the longitudinal axis of the housing portion 34 effects articulation of the end effector 50 about a pivot member or pin 42. This pivotal movement can be controlled by the actuation lever 26 of the handle assembly 28, with components being disposed between the lever 26 and the mounting assembly 40 to allow for movement of the lever 26 to articulate the mounting assembly 40, and thereby the end effector 50. Similar to the firing system of the instrument 10, a person skilled in the art will recognize various configurations of components for effecting articulation, mechanical or otherwise, and thus a detailed explanation of the same is unnecessary. Some exemplary embodiments of components for effecting articulation that are suitable for use with the disclosures herein are provided for in patents and patent applications incorporated by reference elsewhere in the present application.

Figure 6:
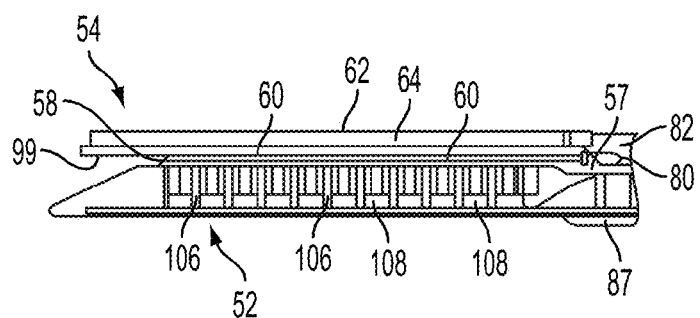
FIG. 6 is a side cross-sectional view taken along the section line indicated in FIG. 5.

The end effector 50 of the illustrated embodiment is a surgical stapling tool having a first, lower jaw 52 that serves as a cartridge assembly or carrier and an opposed second, upper jaw 54 that serves as an anvil. As shown in FIG. 6, an inner surface 58 of the second jaw 54, sometimes referred to as an anvil portion, can include a plurality of staple deforming cavities 60 and a cover plate 62 secured to a top surface 59 of the jaw 54 to define a cavity 64 therebetween. The cover plate 62 can help to prevent pinching of tissue during clamping and firing of the surgical stapler. The cavity 64 can be dimensioned to receive a distal end 80d of the axial drive assembly 80. A longitudinal slot 66 can extend through the anvil portion 58 to facilitate passage of a retention flange 82 of the axial drive assembly 80 into the anvil cavity 64. A camming surface 57 formed on the anvil portion 58 can be positioned to engage the axial drive assembly 80 to facilitate clamping of tissue 99. A pair of pivot members 53 formed on the anvil portion 54 can be positioned within slots 51 formed in the carrier 52 to guide the anvil portion between the open and clamped positions. A pair of stabilizing members can engage a respective shoulder 55 formed on the carrier 52 to prevent the anvil portion 54 from sliding axially relative to the staple cartridge 100 as the camming surface 57 is deformed. In other embodiments, the carrier 52 and staple cartridge 100 can be pivoted between open and clamped positions while the anvil portion 54 remains substantially stationary.

Figure 5:
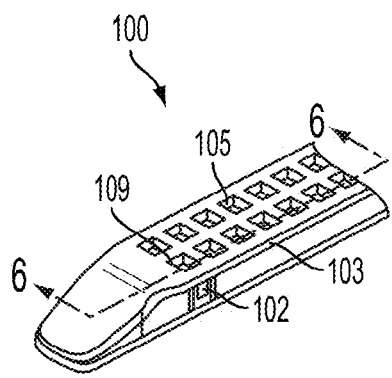
FIG. 5 is a detailed perspective view of a distal end of a staple cartridge for use with the end effector of FIG. 4.
Figure 7:
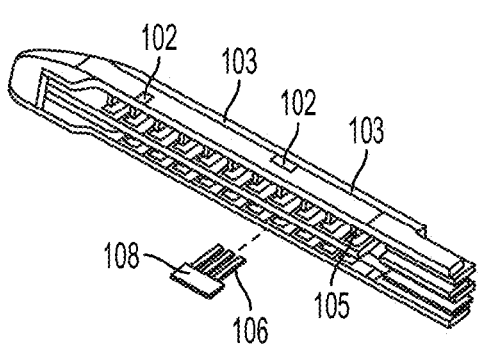
FIG. 7 is a bottom perspective view of the staple cartridge of FIG. 5.
Figure 8:
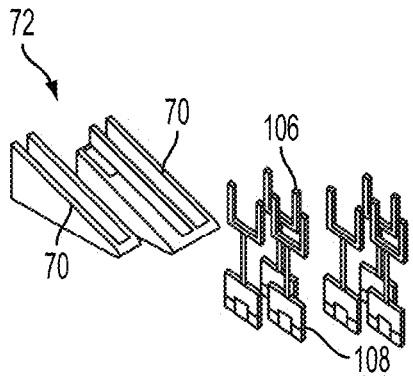
FIG. 8 is an exploded perspective view of an actuation sled, pushers, and fasteners of the surgical instrument of FIG. 4.

The elongated support channel 56 of the first jaw 52 can be dimensioned and configured to receive a staple cartridge 100, as shown in FIGS. 4, 5, and 7. Corresponding tabs 102 and slots 68 formed along the staple cartridge 100 and the elongated support channel 56, respectively, function to retain the staple cartridge 100 within the support channel 56. A pair of support struts 103 formed on the staple cartridge 100 can be positioned to rest on sidewalls of the carrier 52 to further stabilize the staple cartridge 100 within the support channel 56. The staple cartridge 100 can also include retention slots 105 for receiving a plurality of fasteners 106 and pushers 108. A plurality of spaced apart longitudinal slots 107 can extend through the staple cartridge 100 to accommodate upstanding cam wedges 70 of an actuation sled 72 of a firing system (FIGS. 4 and 8). A central longitudinal slot 109 can extend along the length of the staple cartridge 100 to facilitate passage of a knife blade 81 associated with the axial drive assembly 80. During operation of the surgical stapler, the actuation sled 72 translates through longitudinal slots 107 of the staple cartridge 100 to advance cam wedges 70 into sequential contact with pushers 108, thereby causing the pushers 108 to translate vertically within the retention slots 105 and urge the fasteners 106 from the slots 105 into the staple deforming cavities 60 of the anvil portion 54.

Figure 9:
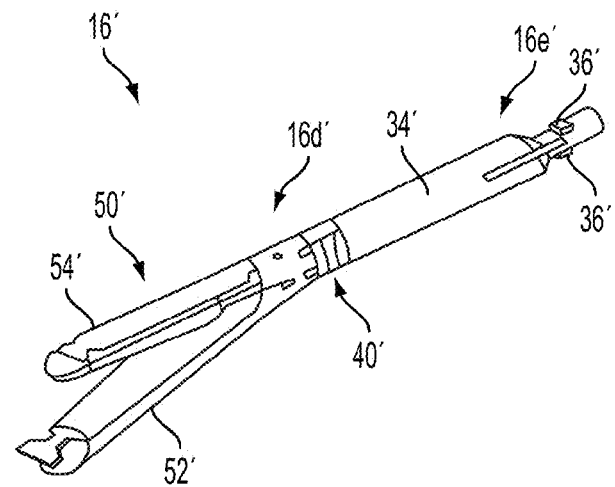
FIG. 9 is a perspective view of another exemplary embodiment of an attachment portion for use a surgical instrument.
Figure 10:
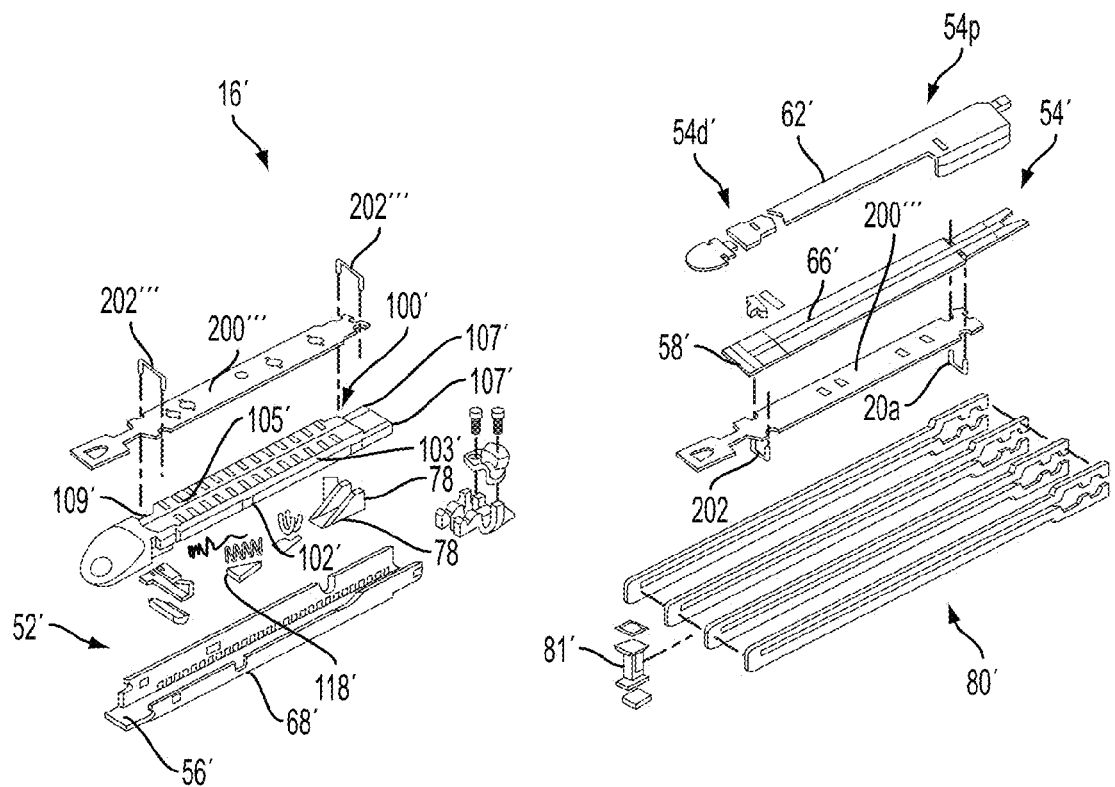
FIG. 10 is an exploded perspective view of an end effector of the attachment portion of FIG. 9.

An alternative embodiment of an attachment portion 16' is shown in FIGS. 9 and 10. The attachment portion 16' can include a proximal housing portion 34' at a proximal end 16p' thereof and an end effector or tool 50' at a distal end 16d' thereof. Nubs 36' can be provided to removably couple the attachment portion 16' to a shaft of a surgical instrument, and a mounting assembly 40' can be provided to removably and/or pivotally couple an end effector or tool 50' to the proximal housing portion 34'. The end effector 50' can include a first, lower jaw 52' that serves as a cartridge assembly, and a second, upper jaw 54' that serves as an anvil portion. The first jaw 52' can have many of the same features as the first jaw 52 of FIGS. 3, 4, and 6, and thus can include an elongated support channel 56' that is dimensioned and configured to receive a staple cartridge 100', and slots 68' configured to correspond with tabs 102' of the staple cartridge 100' to retain the cartridge 100' within the channel 56'. Likewise, the cartridge 100' can include support struts 103' to rest on sidewalls of the jaw 52', retention slots 105' for receiving a plurality of fasteners 106' and pushers 108', a plurality of spaced apart longitudinal slots 107' to accommodate upstanding cam wedges 70' of an actuation sled 72' of a firing system, and a central longitudinal slot 109' to facilitate passage of a knife blade 81' associated with an axial drive assembly 80'.

Similar to the second jaw 54 of FIGS. 3, 4, and 6, the second jaw 54' can include a cover plate 62' secured to a top surface of the jaws to define a cavity therebetween. An anvil plate 58' can serve as the inner surface of the jaw 54', and can include a longitudinal slot 66' for receiving a distal end of the axial drive assembly 80', and a plurality of staple deforming pockets or cavities (not shown) to form staples ejected from the cartridge 100'. In this embodiment, however, the lower jaw 52' containing the cartridge 100' is configured to pivot toward the upper jaw 54' while the upper jaw 54' remains substantially stationary upon actuation by a handle assembly and related components.

Figure 11:
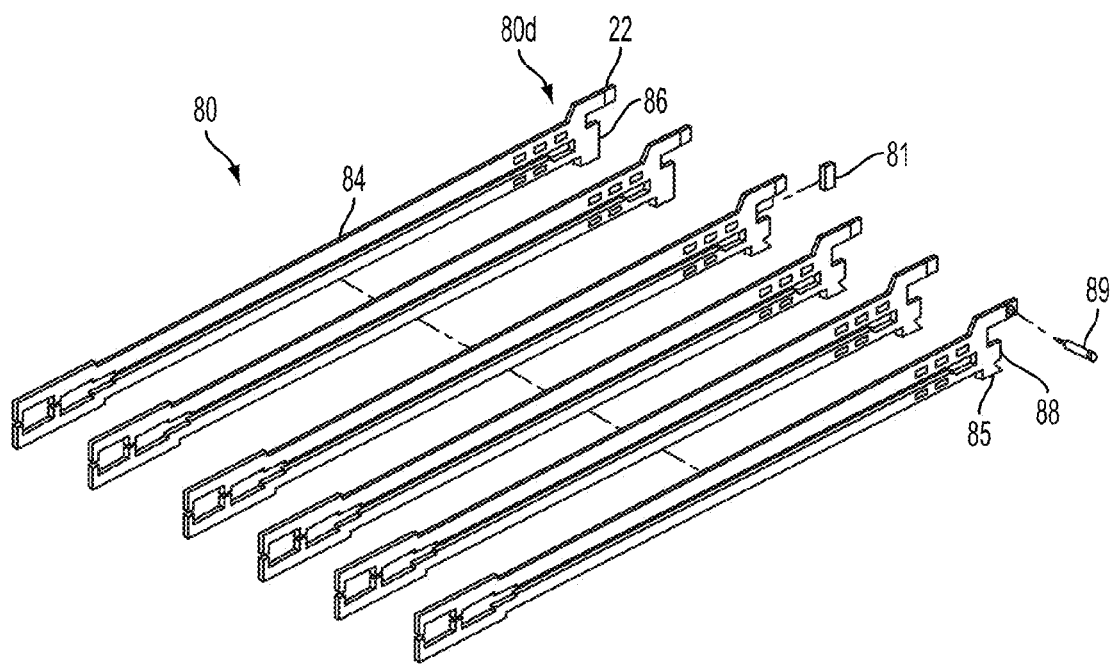
FIG. 11 is an exploded view of a drive assembly for use with the end effector of FIG. 4.

The end effector and staple cartridge disposed therein is configured to receive an axial drive assembly. One non-limiting exemplary embodiment of the axial drive assembly 80 is illustrated in FIG. 11. As shown, a distal end of a drive beam 84 can be defined by a vertical support strut 86 that supports the knife blade 81, and an abutment surface 88 configured to engage the central portion of the actuation sled 72 during a stapling procedure. Bottom surface 85 at the base of the abutment surface 88 can be configured to receive a support member 87 slidably positioned along the bottom of the staple cartridge 100 (FIGS. 4 and 6). The knife blade 81 can be positioned to translate slightly behind the actuation sled 72 through the central longitudinal slot 109 in the staple cartridge 100 to form an incision between rows of stapled body tissue. The retention flange 82 can project distally from the vertical strut 86 and can support a cylindrical cam roller 89 at its distal end. The cam roller 89 can be dimensioned and configured to engage the camming surface 57 on the anvil portion 58 to clamp the anvil portion 58 against body tissue. A person skilled in the art will recognize that a drive assembly for use in conjunction with surgical staplers or other surgical instruments can have many other configurations than the one illustrated in FIG. 11, some of which are described in patents and patent applications incorporated by reference elsewhere in the present application. By way of non-limiting example, the drive assembly 80 can include a single drive beam, or any other number of drive beams, and the distal end of the drive beam(s) can have any number of shapes that are configured for use in the end effector through which the drive assembly is configured to travel.

In use, the surgical stapler can be disposed in a cannula or port and disposed at a surgical site. A tissue to be cut and stapled can be placed between the jaws 52, 54 of the surgical stapler 10. Features of the stapler 10, such as the rotating knob 24 and the actuation lever 26, can be maneuvered as desired by the clinician to achieve a desired location of the jaws 52, 54 at the surgical site and the tissue with respect to the jaws 52, 54. After appropriate positioning has been achieved, the trigger 20 can be pulled toward the stationary handle 22 to actuate the firing system. The trigger 20 can cause components of the firing system to operate such that the control rod 32 advances distally through at least a portion of the shaft 14 to cause at least one of the jaws 52, 54 to collapse towards the other to clamp the tissue disposed therebetween and/or to drive the drive assembly 80 distally through at least a portion of the end effector 50.

In some embodiments, a first firing of the trigger 20 can cause the jaws 52, 54 to clamp the tissue, while subsequent firings of the trigger 20 can cause the drive assembly 80 to be advanced distally through at least a portion of the end effector 50. A single, subsequent firing can fully advance the drive assembly 80 through the staple cartridge 100 to eject the staples in the row, or alternatively, the components in the handle assembly 12 can be configured such that multiple, subsequent firings are required to fully advance the drive assembly 80 through the staple cartridge 100 to eject the staples in the row. Any number of subsequent firings can be required, but in some exemplary embodiments anywhere from two to five firings can fully advance the drive assembly 80 through the staple cartridge 100. In embodiments in which the drive assembly 80 includes the knife 81 to cut the tissue being stapled, the knife 81 cuts tissue as the drive assembly advances distally through the end effector 50, and thus the staple cartridge 100 disposed therein. In other exemplary embodiments, a motor disposed within the handle assembly 12 and associated with a firing trigger can actuate the drive assembly 80 automatically in response to activation of the firing trigger.

After the drive assembly 80 has been advanced distally through the staple cartridge 100, the retraction knobs 28 can be advanced proximally to retract the drive assembly 80 back towards its initial position. In some configurations, the retraction knobs 28 can be used to retract the drive assembly 80 prior to fully advancing the assembly 80 through the cartridge 100. In other embodiments retraction of the drive assembly 80 can be automated to occur after a predetermined action. For example, once the drive assembly 80 has distally advanced to its desired location, the subsequent return of the trigger 80 back to a biased open position can cause the drive assembly 80 to automatically retract. A motor and associated components, rather than retraction knobs 28 and associated components, can be used to retract the drive assembly 80. Further, as discussed above, other features, such as a firing lockout mechanism, an anti-reverse clutch mechanism, and an emergency return button, can be relied upon during operation of the surgical stapler 10, as would be understood by those skilled in the art.

The illustrated embodiment of a surgical stapling instrument 10 provides one of many different configurations, and associated methods of use, that can be used in conjunction with the disclosures provided herein. Additional exemplary embodiments of surgical staplers, components thereof, and their related methods of use, that can be used in accordance with the present disclosure include those devices, components, and methods provided for in U.S. Patent Application Publication No. 2012/0083835 and U.S. Patent Application Publication No. 2013/0161374, each of which is incorporated by reference herein in its entirety.

Implantable Materials

Figure 12:
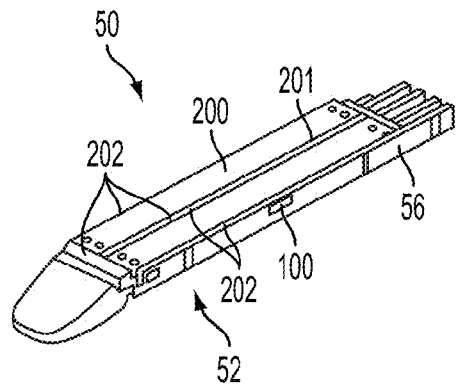
FIG. 12 is a perspective view of a lower jaw of the end effector of FIG. 3.
Figure 13:
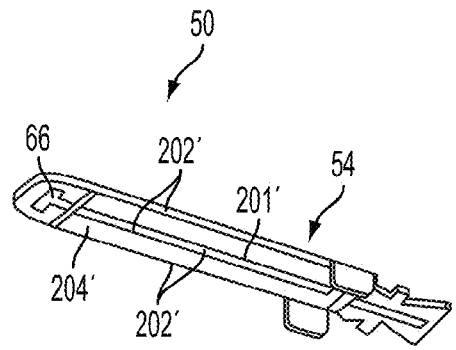
FIG. 13 is a perspective view of an upper jaw of the end effector of FIG. 3, the upper jaw having an adjunct material associated therewith.

Regardless of the configuration of the surgical instrument, the present disclosure provides for the use of implantable materials, e.g., biologic materials and/or synthetic materials, collectively "adjunct materials," in conjunction with instrument operations. As shown in FIGS. 12 and 13, the end effector 50 can include at least one piece of adjunct material 200, 200' positioned intermediate the first and second jaw members 52, 54 and it can be releasably retained to one of the support channel 56 and/or the anvil portion 58. In the illustrated embodiment, the releasable retention is provided by retention members 202, 202', which are described in further detail below. In at least one embodiment, a surface on the adjunct material 200, 200' can be configured to contact tissue as the tissue is clamped between the first and second jaw members 52, 54. In such an embodiment, the adjunct material can be used to distribute the compressive clamping force over the tissue, remove excess fluid from the tissue, and/or improve the purchase of the staples. In various embodiments, one or more pieces of adjunct material can be positioned within the end effector 50. In at least one embodiment, one piece of adjunct material 200 can be attached to the staple cartridge 100 (FIG. 12) and one piece of adjunct material 200' can be attached to the anvil portion 58 (FIG. 13). In at least one other embodiment, two pieces of adjunct material 200 can be positioned on the support channel 56 and one piece of adjunct material 200' can be positioned on the anvil portion 58, for example. Any suitable number of adjunct materials can be situated within the end effector 50.

Adjunct material used in conjunction with the disclosures provided for herein can have any number of configurations and properties. Generally, they can be formed from of a bioabsorbable material, a biofragmentable material, and/or a material otherwise capable of being broken down, for example, such that the adjunct material can be absorbed, fragmented, and/or broken down during the healing process. In at least one embodiment, the adjunct material can include a therapeutic drug that can be configured to be released over time to aid the tissue in healing, for example. In further various embodiments, the adjunct materials can include a non-absorbable and/or a material not capable of being broken down, for example. Similarly, the connection members can be at least partially fondled from at least one of a bioabsorbable material, a biofragmentable material, and a material capable of being broken down such that the connection members can be absorbed, fragmented, and/or broken down within the body. In various embodiments, the connection members can include a therapeutic drug that can be configured to be released over time to aid the tissue in healing, for example. In further various embodiments, the connection members can include a non-absorbable and/or a material not capable of being broken down, for example, such as a plastic.

More particularly, some exemplary, non-limiting examples of synthetic materials that can be used in conjunction with the disclosures provided for herein include biodegradable synthetic absorbable polymer such as a polydioxanone film sold under the trademark PDS or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), or a blend of copolymerization of the PGA, PCL, PLA, PDS monomers. In use, the synthetic material can be broken down by exposure to water such that the water attacks the linkage of a polymer of the synthetic material. As a result, the mechanical strength can become diminished, and a construct of the material can be broken down into a mushy or fractured scaffold. As further breakdown occurs such that the material breaks into carbohydrates and acid constituents, a patient's body can metabolize and expel the broken down materials.

Some exemplary, non-limiting examples of biologic derived materials that can be used in conjunction with the disclosures provided for herein include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized cellulose, mussel-based adhesive, poly (amino acid), agarose, polyetheretherketones, amylose, hyaluronan, hyaluronic acid, whey protein, cellulose gum, starch, gelatin, silk, or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Patent Application Publication No. 2012/0080335, U.S. Patent Application Publication No. 2012/0083835, U.S. patent application Ser. No. 13/433,115, entitled "Tissue Thickness Compensator Comprising Capsules Defining a Low Pressure Environment," and filed on Mar. 28, 2012, U.S. patent application Ser. No. 13/433,118, entitled "Tissue Thickness Compensator Comprised of a Plurality of Materials," and filed on Mar. 28, 2012, U.S. patent application Ser. No. 13/532,825, entitled "Tissue Thickness Compensator Having Improved Visibility," and filed on Jun. 26, 2012, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one of a component of the end effector and the staple cartridge prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

Retention Members

Connection or retention members can be used to secure, at least temporarily, one or more pieces of adjunct material onto an end effector and/or staple cartridge. These retention members can come in a variety of forms and configurations, such as one or more sutures, adhesive materials, staples, brackets, snap-on or other coupling or mating elements, etc. For example, the retention members can be positioned proximate to one or more sides and/or ends of the adjunct material, which can help prevent the adjunct material from peeling away from the staple cartridge and/or the anvil face when the end effector is inserted through a trocar or engaged with tissue. In still other embodiments, the retention members can be used with or in the form of an adhesive suitable to releasably retain the adjunct material to the end effector, such as cyanoacrylate. In at least one embodiment, the adhesive can be applied to the retention members prior to the retention members being engaged with the adjunct material, staple cartridge, and/or anvil portion. Generally, once firing is completed, the retention member(s) can be detached from the adjunct material and/or the end effector so that the adjunct material can stay at the surgical site when the end effector is removed. Some exemplary, non-limiting embodiments of retention members are described herein with respect to FIGS. 12-15.

FIG. 12 illustrates one exemplary embodiment of a connection or retention member 202 associated with the adjunct material 200 to secure the material 200 at a temporary location with respect to the lower jaw 52 of the end effector 50. As shown, the adjunct material 200 is disposed over the staple cartridge 100 located in the elongate channel 56 of the lower jaw 52, and the retention member 202 extends therethrough. In the embodiment, the retention member 202 is in the form of a single suture stitched through multiple locations of the adjunct material 200, or it can be multiple sutures disposed at one or more locations on the adjunct material 200. As shown, the sutures are positioned at locations around a perimeter of the adjunct material 200, and are also adjacent to a central longitudinal channel 201 formed in the adjunct material 200. The channel 201 can make it easier for a knife passing through the adjunct material 200 to cut the material 200 into two or more separate strips. In some embodiments, for instance when the retention member 202 is a single suture threaded through multiple locations of the adjunct material 200, a knife passing through the lower jaw 52 can cut the retention member 202 at one or more locations, thereby allowing the retention member 202 to be disassociated from the adjunct material 200 and removed from the surgical site while the adjunct material 200 remains held at the surgical site by one or more staples ejected from the cartridge 100.

FIG. 13 illustrates another embodiment of a connection or retention member 202' associated with the adjunct material 200' to secure the material 200' at a temporary location on the end effector 50. The retention member 202' has the same configuration as the retention member 202 in FIG. 12, however, in this embodiment it is used to secure the material to the anvil or upper jaw 54, rather than the cartridge or lower jaw 52.

Figure 14:
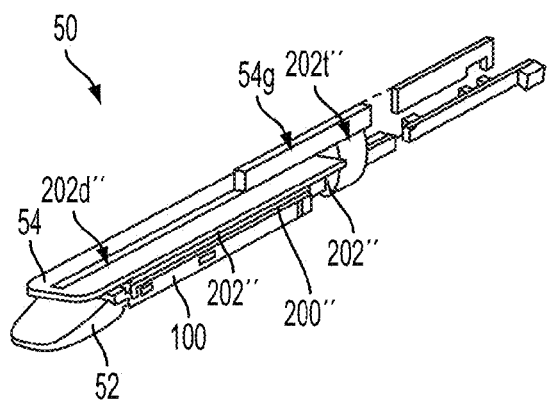
FIG. 14 is a perspective view of portions of the end effector of FIG. 2 including a retention member configured to releasably retain an adjunct material.

FIG. 14 illustrates another, non-limiting embodiment of a connection or retention member 202" used to releasably retain an adjunct material 200" to at least one of the upper jaw 54 and the lower jaw 52. In this embodiment, the retention member 202" is a single suture that extends through a distal portion 200d" of the adjunct material 200" and is coupled to a proximal end 54p of the upper jaw 54. Terminal ends 202t" of the retention member 202" can be used to move the retention member 202" with respect to the jaws 54, 52. In its extended position, which is illustrated in FIG. 14, the retention member 202" can hold the adjunct material 200" in position as the end effector 50 is inserted into a surgical site. Thereafter, the jaws 52, 54 of the end effector 50 can be closed onto tissue, for example, and staples from the staple cartridge 100 can be deployed through the adjunct material 200" and into the tissue. The retention member 202" can be moved into its retracted position such that the retention member 202" can be operably disengaged from the adjunct material 200". Alternatively, the retention member 202" can be retracted prior to the staples being deployed. In any event, as a result of the above, the end effector 50 can be opened and withdrawn from the surgical site leaving behind the adjunct material 200" and tissue.

Figure 15:
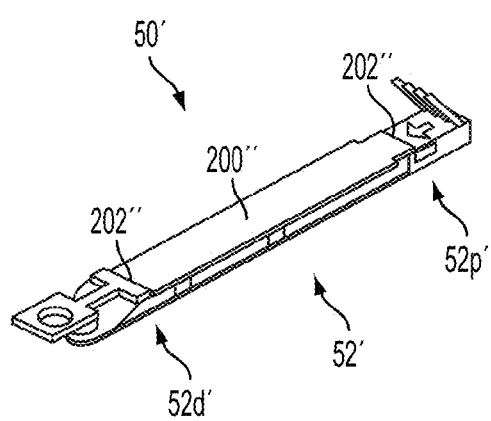
FIG. 15 is a perspective view of a lower jaw of the end effector of FIG. 10.

FIG. 15 illustrates yet another, non-limiting embodiment of a connection or retention member 202''' for securing a location of adjunct material 200''' to an end effector. In particular, the adjunct material 200''' and retention member 202''' are used in conjunction with the end effector 50' of FIGS. 9 and 10. In this embodiment, the retention member 202''' is in the form of a suture that is used to tie the adjunct material 200''' to the first, lower jaw 52' at proximal and distal ends thereof 52p', 52d'. Similarly, as shown in FIGS. 9 and 10, the adjunct material 200''' can also be secured to the second, upper jaw 54' at proximal and distal ends thereof 54p', 54d'. Optionally, recesses can be formed in either or both of the jaws 52', 54', and either or both of the adjunct materials 200''', which can protect the retention members 202''' against unintended cutting by an outside object. In use, the knife blade 81' on the driver assembly 80' can incise the retention members 202''' as it passes through the end effector 50' to release the adjunct material 200'''.

A person skilled in the art will recognize a variety of other ways by which the adjunct material can be temporarily retained with respect to the end effector. In various embodiments a connection or retention member can be configured to be released from an end effector and deployed along with a piece of adjunct material. In at least one embodiment, head portions of retention members can be configured to be separated from body portions of retention members such that the head portions can be deployed with the adjunct material while the body portions remain attached to the end effector. In other various embodiments, the entirety of the retention members can remain engaged with the end effector when the adjunct material is detached from the end effector.

Tissue Ingrowth Materials

As indicated above, various adjunct materials are provided for use with a surgical stapler. While in some instances the adjunct materials can be a synthetic material and/or a biologic material, in some exemplary embodiments the adjunct material can be especially configured to facilitate tissue ingrowth into the materials. While this can be achieved using various techniques, in one embodiment the adjunct material can include both hydrophilic portions and hydrophobic portions to form a hydrophilic-hydrophobic adjunct material. The resulting combination can advantageously have surfaces or portions that attract cells and encourage cell ingrowth (hydrophilic) and surfaces or portions that do not attract cells or otherwise encourage cell ingrowth (hydrophobic). In use, the hydrophilic portions can be placed in contact with the tissue, while the hydrophobic portions can be oriented away from the tissue surface.

In certain embodiments, synthetic polymers used to form adjunct materials can be hydrophobic, such as polycaprolactone (PCL) and polylactic acid (PLLA). It is noted that "polymers" as used herein can include copolymers. Synthetic adjunct materials, however, can be treated or otherwise produced to be hydrophilic, as will be discussed herein. To form the adjunct material, any method of creating a synthetic material having a hydrophilic portion and a hydrophobic portion can be used. In some embodiments, a surface of (or only half of) a hydrophobic adjunct material is treated with an acid or base which can cause the formation of pockets or pits in the surface. Alternatively, the adjunct material can be formed by bonding a hydrophilic layer to a hydrophobic layer. For example, an adjunct material can be treated such that the entire adjunct material becomes hydrophilic. Then this hydrophilic layer can be bound, such as by laminating, to a second hydrophobic adjunct material layer creating a material that is hydrophobic and hydrophilic. Various approaches can be used to create an adjunct material or matrix where a tissue contacting portion encourages cellular ingrowth while a non-tissue contacting portion discourages cellular ingrowth.

Any adjunct material, such as those described above, can be made hydrophilic and/or hydrophobic. Additionally, a person skilled in the art will appreciate that any form of adjunct material can be made to be hydrophilic and/or hydrophobic, for example a film type adjunct material and/or a foam type adjunct material. In one exemplary embodiment, a film or foam can be made hydrophilic using any suitable technique, such as surface grafting techniques and coating techniques, depending upon the physical or chemical characteristics of the film or foam.

Surface grafting techniques can be employed, for example, if the film or foam has reactive chemical sites or functionalities such as amino, hydroxyl or carboxyl groups. If this is the case, the film or foam can be made hydrophilic by covalently binding hydrophilic moieties or surfactants onto the film or foam. These hydrophilic moieties can include, but are not limited to, polyethylene glycol (PEG) and poloxamers (available under the trade names Pluronic® available from BASF, Synperonic® available from Sigma Aldrich, and Kolliphor available from BASF).

Coating techniques can be used, for example, if the film or foam does not have any reactive sites as it will generally not be possible to impart the hydrophilic characteristics using surface grafting techniques. Various levels of coating with a hydrophilic polymer will impart varying degrees of hydrophilicity to the foam or film. However, care needs to be taken in the case of porous foam since coating can result in closing of the open pores and may result in conversion of open cell or reticulated foam to closed cell foam.

In one embodiment, hydrophilic 65:35 PGA/PCL polymers can be prepared by copolymerizing PEG/Pluronic with PCL/PGA. Introduction of PEG or poloxamer repeat units in the copolymer backbone can render the backbone hydrophilic resulting in swelling upon contact with body fluids including blood. The hydrophilicity of the polymer can be controlled by using various molecular weights of PEG and poloxamers and the ratio of PEG/poloxamer to PCL/PGA. For example, higher content of PEG/poloxamer is expected to result in higher swelling and higher hydrophilicity.

Figure 16:
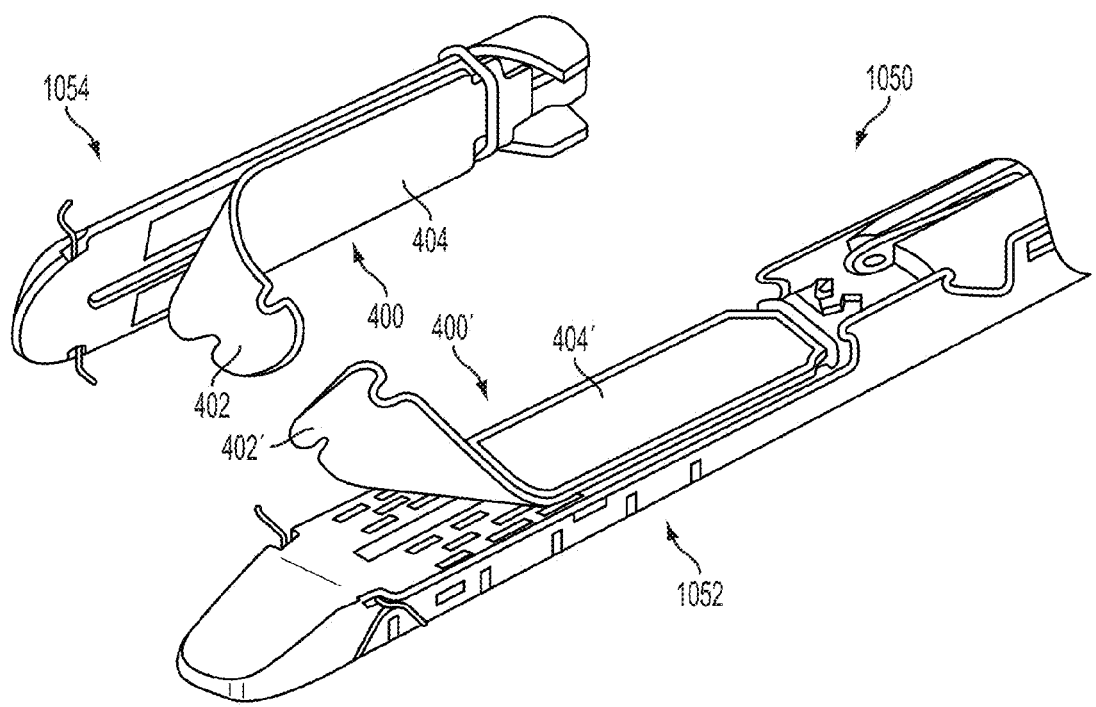
FIG. 16 is a perspective view of portions of an end effector having an adjunct material associated therewith.

An adjunct material can be selectively attached to either or both jaws of an end effector. As shown in FIG. 16, an adjunct material 400, 400' can be attached to both lower and upper jaws 1052, 1054 of an end effector 1050. The adjunct material 400, 400' can have a first side 402, 402' that is hydrophobic and a second side 404, 404' that is hydrophilic. The first, hydrophobic side 402, 402' can be configured to face and directly contact the upper and lower jaws 1052, 1054, while the second, hydrophilic side 404, 404' can be oriented away from the upper and/or lower jaws 1052, 1054. In this configuration, the second hydrophilic side 404, 404' will face and directly contact the tissue being treated (i.e., grasped by the end effector 1050) once the end effector 1052 is actuated, and the first, hydrophobic side 402, 402' will be on an opposite side facing away from the tissue being treated or grasped. This configuration is illustrated in FIGS. 18A and 18B, as will be discussed in detail below.

Figure 17A:
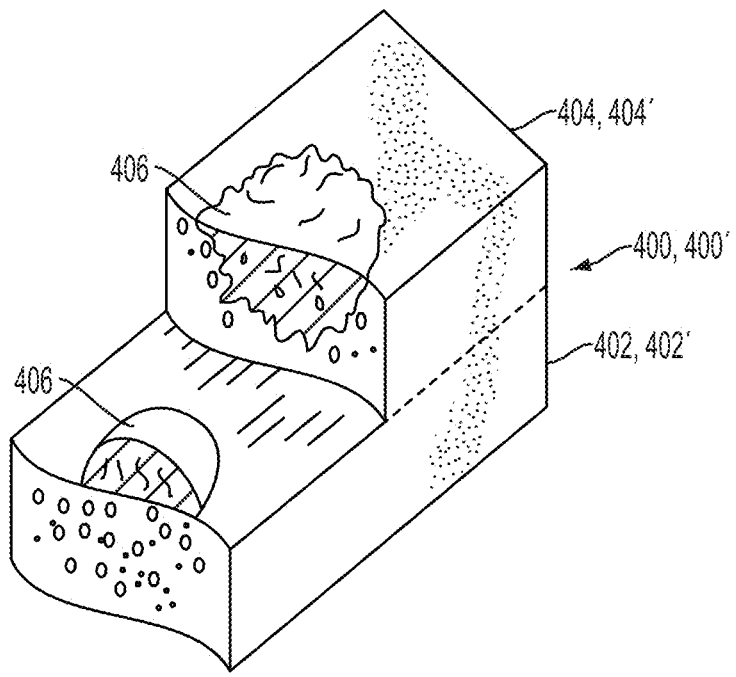
FIG. 17A is a partial cutaway view of an exemplary adjunct material having a drop of water disposed thereon.
Figure 17B:
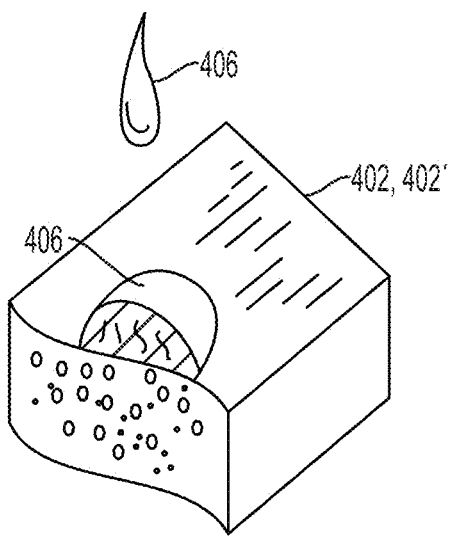
FIG. 17B is a partial cutaway view of an exemplary hydrophobic adjunct material having a drop of water disposed thereon.
Figure 17C:
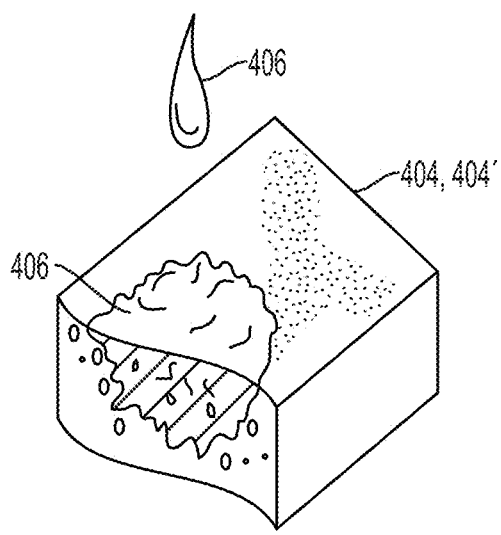
FIG. 17C is a cross-sectional view of an exemplary hydrophilic adjunct material having a drop of water disposed thereon.

FIGS. 17A-17C illustrate the adjunct material 400, 400' when wetted by a drop of water 406. As shown, the hydrophilic side 404, 404' absorbs the water 406 and disperses the water 406 through the layer 404, 404'. In contrast, the hydrophobic side 402, 402' repels the water 406, which remains substantially on the surface of the hydrophobic layer 402, 402'.

Figure 18A:
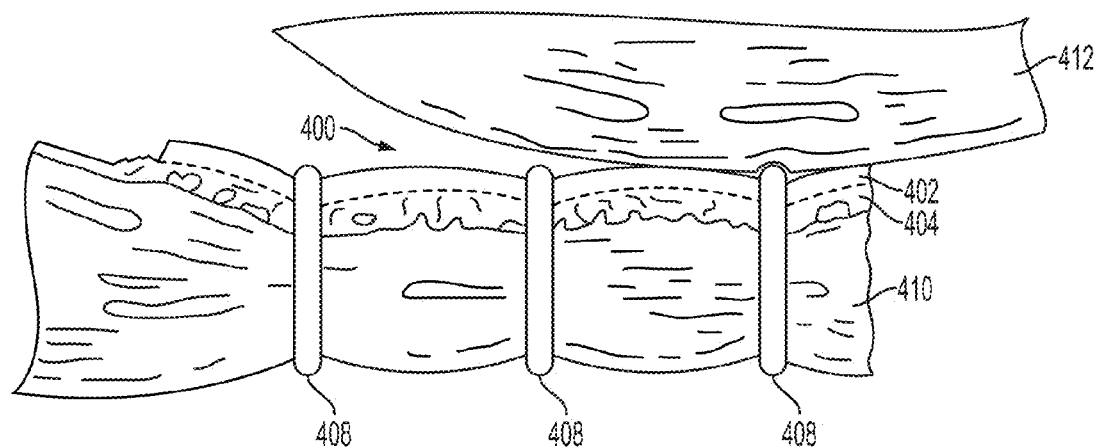
FIG. 18A is a side view of an adjunct material maintained adjacent a tissue to be treated and an adjacent organ by staples.
Figure 18B:
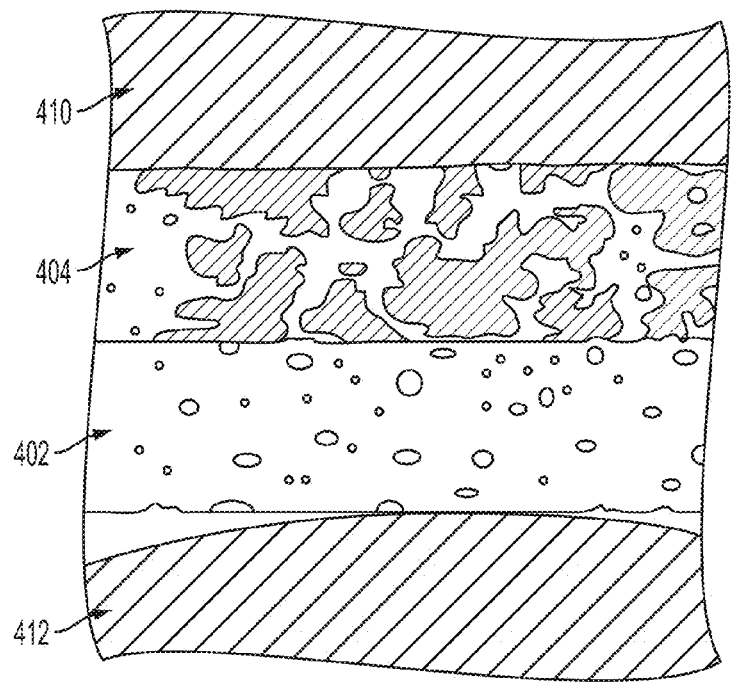
FIG. 18B is a cross-sectional view of an exemplary adjunct material disposed between a tissue to be treated and an adjacent organ.

In use, the adjunct material 400 can be positioned in a body, such as is shown in FIGS. 18A and 18B. As shown in FIG. 18A, the adjunct material 400 is implanted at a treatment site using staples 408 such that the hydrophilic side 404 of the adjunct material 400 is directly contacting the tissue to be treated 410 and the hydrophobic side 402 on an opposite side and is exposed to an adjacent tissue 412, such as an organ where tissue ingrowth is not desired. In this configuration, the hydrophilic side 404 enhances cellular ingrowth into the grasped tissue 410 and the hydrophobic side 402 discourages cellular ingrowth and therefore prevents the hydrophobic side from attaching to adjacent tissue 412. FIG. 18B illustrates this further as the hydrophilic side 404 is in contact with the tissue to be treated 410, but not the adjacent tissue 412 and the hydrophobic side is in contact with the adjacent tissue 412, but not the tissue to be treated 410.

Biologically Coated Synthetic Materials

As mentioned above, typically synthetic absorbable materials are hydrophobic and at best do not inhibit healing and at worst are treated like foreign bodies during healing. It is possible, however, to take a hydrophobic matrix, like PGA/PCL, and micro-etch or pit the surface of the polymer to make the material more hydrophilic. Once etched or pitted, it is further possible to deposit or coat the synthetic absorbable material with a biologic material, such as collagen or fibrin, so as to form an synthetic absorbable material that has a biologic coating, which enhances healing as a biologic but retains the structural properties of the synthetic absorbable material.

Figure 19A:
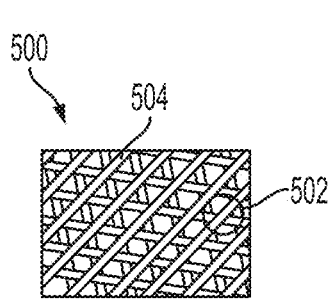
FIG. 19A is a perspective view of an exemplary adjunct material having surface features.
Figure 19B:
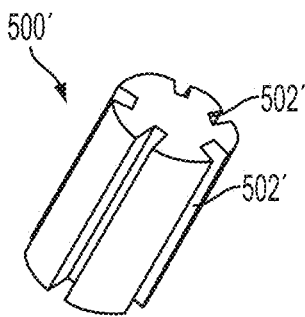
FIG. 19B is a perspective view of another exemplary adjunct material having surface features.
Figure 19C:
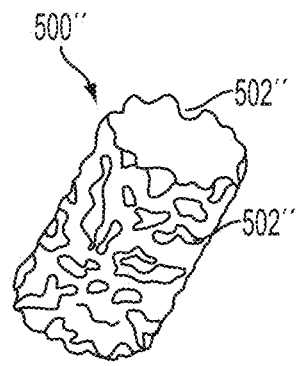
FIG. 19C is a perspective view of yet another exemplary adjunct material having surface features.

FIGS. 19A-19C illustrate various synthetic absorbable materials having surface features and characteristics, such as nanofeatures, that create a macro-structure that has the effect of creating a hydrophilic surface thus allowing for biologic coating. FIG. 19A depicts an adjunct material that is woven 500. The woven material creates surface features 502, i.e., pockets, that can entrap a biologic. Additionally, the woven adjunct material 500 can be formed of fibers 504 that are either hydrophilic or hydrophobic, or combinations thereof, which allow the woven material to be an hydrophilic-hydrophobic material, as well as enables it to have a biologic coating. FIG. 19B depicts a synthetic absorbable material 500' that has micro-etched surface features 502' that are produced using a laser etching technique. These surface features 502' similarly provide hydrophilic surface features on the synthetic absorbable material. FIG. 19C illustrates a synthetic absorbable material 500" that has been treated with a surface hydrolysis technique. This surface hydrolysis can be done through introduction of a strong acid or base that is then washed off or freeze dried away before it destroys the entire matrix. This surface hydrolysis results in surface pitting forming a macro-structure that creates a hydrophilic surface and thus encourages cellular ingrowth. Likewise weaving, laser etching, surface coating, plasma treatment, surface grafting, and/or blending can be done to improve the hydrophilic properties of the synthetic absorbable material. These surface etching and pitting techniques can not only make the adjunct material (or scaffold) hydrophilic, it can leave pitted surfaces that retain fluids once they are encourage to move into the structure.

Figure 20A:
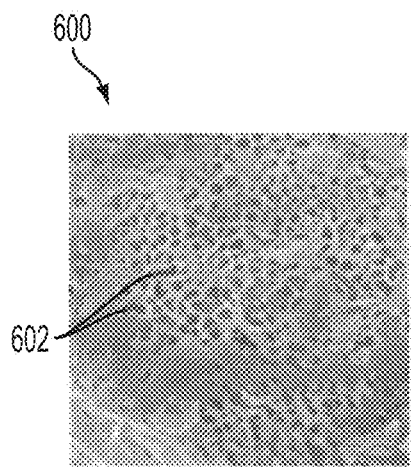
FIG. 20A is a scanning electron microscope image of an exemplary adjunct material having surface features.
Figure 20B:
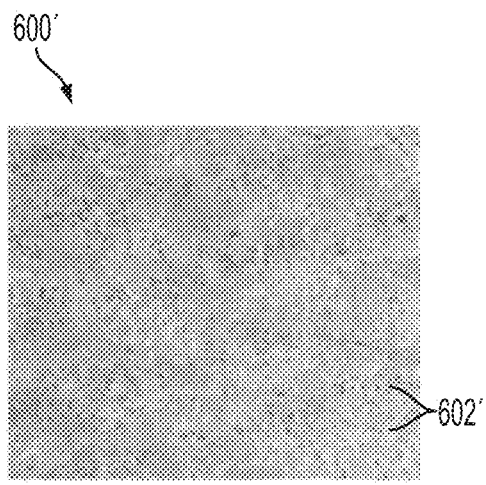
FIG. 20B is a scanning electron microscope image of another exemplary adjunct material having surface features.
Figure 20C:
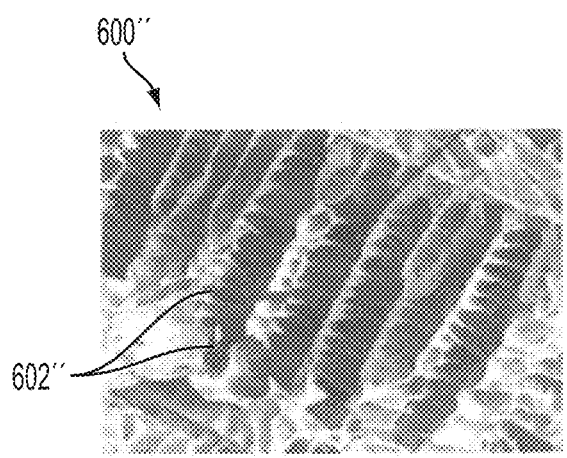
FIG. 20C is a scanning electron microscope image of yet another exemplary adjunct material having surface features.
Figures 21A, 21B, 21C:
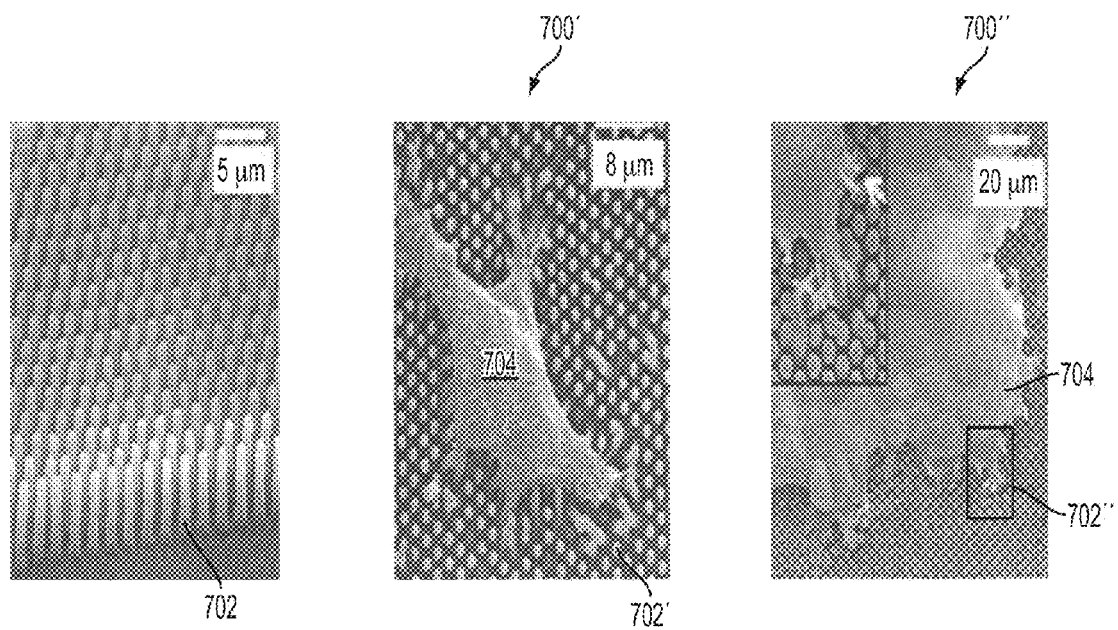
FIG. 21A is a scanning electron microscope image of an exemplary adjunct material having surface features.
FIG. 21B is a scanning electron microscope image of another exemplary adjunct material having surface features.
FIG. 21C is a scanning electron microscope image of yet another exemplary adjunct material having surface features'
Figures 22A, 22B, 22C:
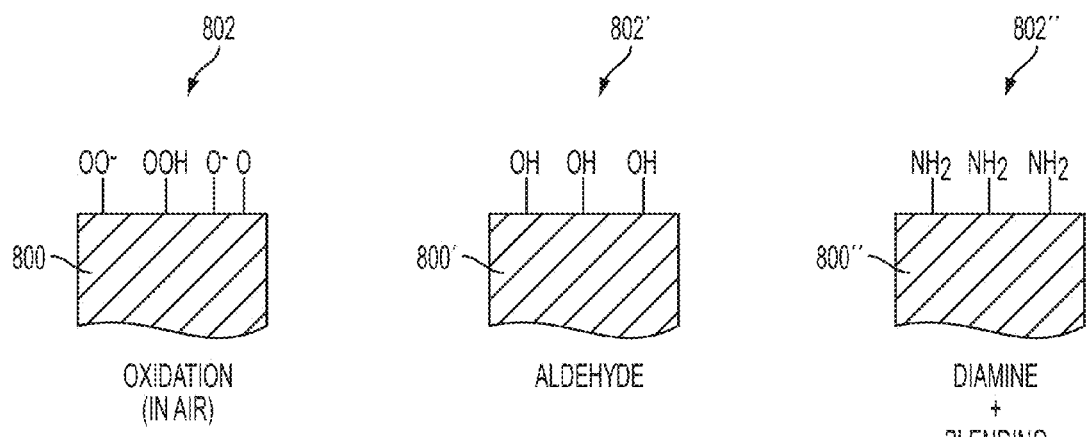
FIG. 22A is a perspective view of an exemplary adjunct material having surface features.
FIG. 22B is a perspective view of another exemplary adjunct material having surface features.
FIG. 22C is a perspective view of yet another exemplary adjunct material having surface features.

FIGS. 20A-20C are scanning electron microscope images of synthetic absorbable materials 600, 600', 600" having surface pitting 602, 602', 602". FIGS. 21A-21C are scanning electron microscope images of synthetic absorbable materials 700, 700', 700" having micro-etched nanofeatures 702, 702', 702" on their surface. As shown in FIGS. 21B and 21C, cells 704 adhere or attach to the nanofeatures 702', 702" and thus encourage cellular ingrowth. FIGS. 22A-22C illustrate additional surface features, i.e., function groups, 802, 802', 802" that can be formed on synthetic absorbable material 800, 800', 800" using plasma etching and/or polymer etching techniques. FIG. 22A shows the result of plasma etching and/or polymer grafting that occurs when oxidation in air occurs, FIG. 22B shows that hydroxyl groups 802' are formed when an aldehyde is used, and FIG. 22C shows that amine groups 802" are formed when diamines and blending are used.

Coating the micro-etched or pitted synthetic absorbable material can be achieved by any suitable method. For example, once the pitted or etched surface is formed, it can be saturated with a liquified collagen, fibrin, or other biologic material. Following saturation, the saturated synthetic absorbable adjunct material or scaffold can then be freeze dried or lyophilized to create a biologic surface coating that will be retained in the pits even after hydrating the adjunct material or scaffold. This biologically coated synthetic material can act like a biologic to in growing cells while still retaining desired synthetic properties, as discussed above.

Reuse

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., electrodes, a battery or other power source, an externally wearable sensor and/or housing therefor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Additional exemplary structures and components are described in U.S. application Ser. No. 14/074,884 entitled "Sealing Materials For Use In Surgical Stapling," Ser. No. 14/074,810 entitled "Hybrid Adjunct Materials For Use In Surgical Stapling," Ser. No. 14/075,438 entitled "Positively Charged Implantable Materials And Method Of Forming The Same," and Ser. No. 14/074,902 entitled "Hybrid Adjunct Materials For Use In Surgical Stapling," which are filed on even date herewith and herein incorporated by reference in their entireties.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A kit for stapling tissue, comprising:
   a surgical stapler having an end effector, the end effector having first and second jaws; and
   an adjunct material formed from a synthetic hydrophobic polymer that is 1) treated with an acid or base; or 2) treated with polyethylene glycol (PEG) or poloxamer repeat units to form a hydrophilic-hydrophobic adjunct material, the adjunct material being configured to a) mate to at least one of the jaws of the end effector; place hydrophilic portions of the adjunct material in contact with a tissue; and c) orient hydrophobic portions of the adjunct material away from the tissue.

2. The kit of claim 1, wherein the hydrophobic polymer comprises an absorbable polymer.

3. The kit of claim 1, wherein the hydrophobic polymer is a copolymer selected from the group consisting of polyglycolic acid (PGA)/polycaprolactone (PCL), and polylactic acid (PLA)/polycaprolactone (PCL).

4. The kit of claim 3, wherein the ratio of PGA/PCL is 65:35.

5. The kit of claim 3, wherein treatment with PEG or poloxamer repeat units results in the copolymer swelling upon contact with body fluids.

6. The kit of claim 1, wherein the hydrophobic polymer is woven.

7. The kit of claim 1, wherein said acid or base treatment results in surface pitting forming a macro-structure that creates a hydrophilic surface.

8. A staple cartridge assembly for use with a surgical stapler, comprising:
   a cartridge body having a plurality of staples disposed therein; and
   an adjunct material configured to be coupled to the cartridge and configured to be securely attached to tissue by staples in the cartridge, the adjunct material being formed from a synthetic hydrophobic polymer that is 1) treated with an acid or base; or 2) treated with polyethylene glycol (PEG) or poloxamer repeat units to form a hydrophilic-hydrophobic adjunct material.

9. The assembly of claim 8, wherein the adjunct material is formed from a hydrophobic polymer that is treated with PEG or poloxamer repeat units.

10. The assembly of claim 8, wherein the adjunct material is formed from a hydrophobic polymer that is treated with an acid or base.

11. The assembly of claim 8, wherein hydrophilic portions of the adjunct material are configured to directly contact tissue when secured to tissue by the staples such that tissue ingrowth is encouraged.

12. The assembly of claim 8, wherein the hydrophobic polymer is a copolymer selected from the group consisting of polyglycolic acid (PGA)/polycaprolactone (PCL) and polylactic acid (PLA)/polycaprolactone (PCL).

13. The assembly of claim 12, wherein treatment with PEG or poloxamer repeat units results in the copolymer swelling upon contact with body fluids.

14. The assembly of claim 8, wherein the adjunct material includes an electrically charged material.

15. The assembly of claim 8, wherein said acid or base treatment results in surface pitting forming a macro-structure that creates a hydrophilic surface.

16. The assembly of claim 8, wherein the ratio of PGA/PCL is 65:35.

17. The assembly of claim 8, wherein the hydrophobic polymer is woven.

18. A method for stapling tissue, comprising:
attaching an adjunct material to an end effector on a surgical stapling device, the adjunct material being formed from a synthetic hydrophobic polymer that is 1) treated with an acid or base; or 2) treated with polyethylene glycol (PEG) or poloxamer repeat units to form a hydrophilic-hydrophobic adjunct material, such that a hydrophobic portion on the adjunct material directly contacts the end effector;
engaging tissue between jaws of the end effector such that a hydrophilic portion on the adjunct material directly contacts the tissue; and
actuating the end effector to eject at least one staple from the end effector into the tissue, the at least one staple extending through the adjunct material to attach the adjunct material to the tissue.

19. The method of claim 18, wherein the hydrophobic polymer is a polyglycolic acid (PGA)/polycaprolactone (PCL) copolymer having polyethylene glycol and/or poloxamer repeat units.

* * * * *